(12) United States Patent  (10) Patent No.: US 7,551,711 B2
Sarment et al.  (45) Date of Patent: Jun. 23, 2009

(54) CT SCANNER INCLUDING A CAMERA TO OBTAIN EXTERNAL IMAGES OF A PATIENT

(75) Inventors: David Phillipe Sarment, Ann Arbor, MI (US); Miodrag Rakic, Redondo Beach, CA (US); Neal Clinthorne, Ann Arbor, MI (US); Joseph Webster Stayman, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 11/834,940

(22) Filed: Aug. 7, 2007

(65) Prior Publication Data

US 2008/0031409 A1   Feb. 7, 2008

Related U.S. Application Data

(60) Provisional application No. 60/836,193, filed on Aug. 7, 2006.

(51) Int. Cl.
*A61B 6/00* (2006.01)
(52) U.S. Cl. ............................................. 378/15; 378/4
(58) Field of Classification Search ...................... 378/4, 378/15, 19, 16, 62, 63, 98.2, 197, 205, 206
See application file for complete search history.

(56) References Cited

U.S. PATENT DOCUMENTS

| | | | |
|---|---|---|---|
| 5,023,895 A * | 6/1991 | McCroskey et al. ............. 378/4 |
| 5,662,111 A | 9/1997 | Cosman | |
| 5,836,954 A | 11/1998 | Heilbrun et al. | |
| 6,081,739 A | 6/2000 | Lemchen | |
| 6,088,424 A * | 7/2000 | Postlethwaite et al. ........ 378/63 |
| 6,167,295 A | 12/2000 | Cosman | |
| 6,574,296 B2 * | 6/2003 | Stierstorfer ................... 378/15 |
| 7,203,277 B2 | 4/2007 | Birkenbach et al. | |
| 2002/0067793 A1 | 6/2002 | Stierstorfer | |
| 2003/0083562 A1 | 5/2003 | Bani-Hashemi et al. | |
| 2003/0235266 A1 * | 12/2003 | Gregerson et al. ............. 378/4 |
| 2004/0254456 A1 | 12/2004 | Ritter | |
| 2005/0047552 A1 * | 3/2005 | Arai et al. .................... 378/207 |
| 2006/0281971 A1 * | 12/2006 | Sauer et al. .................. 600/109 |

FOREIGN PATENT DOCUMENTS

| | | |
|---|---|---|
| DE | 10317137 | 11/2004 |
| WO | 2006/071002 | 7/2006 |

OTHER PUBLICATIONS

International Search Report and Written Opinion mailed Feb. 12, 2008.

\* cited by examiner

*Primary Examiner*—Irakli Kiknadze
(74) *Attorney, Agent, or Firm*—Carlson, Gaskey & Olds

(57) ABSTRACT

A CT scanner includes a gantry that supports and houses components of the CT scanner. A camera is mounted to the gantry. As the gantry rotates about an axis of rotation, the camera captures a photographic external image of the patient at a plurality of rotational positions. A computer generates a three dimensional external image from the plurality of external images. The three dimensional external image is registered relative to a three dimensional CT image generated from a plurality of x-ray images.

16 Claims, 3 Drawing Sheets

CT SCANNER INCLUDING A CAMERA TO OBTAIN EXTERNAL IMAGES OF A PATIENT

REFERENCE TO RELATED APPLICATIONS

This application claims priority to U.S. Provisional Application No. 60/836,193 filed Aug. 7, 2006.

BACKGROUND OF THE INVENTION

The present invention relates generally to a CT scanner including a camera located on a gantry that captures photographic external images of a patient to generate a three dimensional external image of the patient.

A CT scanner takes a plurality of x-ray images of a patient to create a three dimensional CT image. A prior art CT scanner system includes a plurality of cameras that take external images of the patient. The cameras are each at a fixed location and do not move during the CT scan. A computer generates a three dimensional external image from the external images taken by the cameras. The three dimensional external image can then be associated with the three dimensional CT image. A drawback to the prior CT scanner is that several cameras are needed to generate the three dimensional photographic image. Additionally, the cameras are difficult to use.

SUMMARY OF THE INVENTION

A CT scanner includes a gantry that supports and houses components of the CT scanner. A first arm houses an x-ray source that generate x-rays, and a second arm houses a complementary flat-panel detector. As the gantry rotates about a patient, the detector takes a plurality of x-ray images at a plurality of rotational positions. A computer generates a three dimensional CT image from the plurality of x-ray images.

In one example, as the gantry rotates about the axis of rotation, a camera mounted to the gantry takes photographic external images of the exterior of the patient. The external images may each correlate to one of the x-ray images. Alternately, each of the external images does not correlate exactly to one of the x-ray images. The x-ray images and the external images are taken at known relative positions. The computer associates each of the external images to one of the x-ray images based on the known relative positions. The computer generates a three dimensional external image from the plurality of external images. The three dimensional external image is registered relative to the three dimensional CT image.

If a technician is viewing the three dimensional CT image on a display and zooms out, the three dimensional CT image changes to the corresponding three dimensional external image. In another example, the three dimensional CT image and the three dimensional external image can be viewed simultaneously on the display side by side.

DETAILED DESCRIPTION OF THE PREFERRED EMBODIMENT

Figure 1:
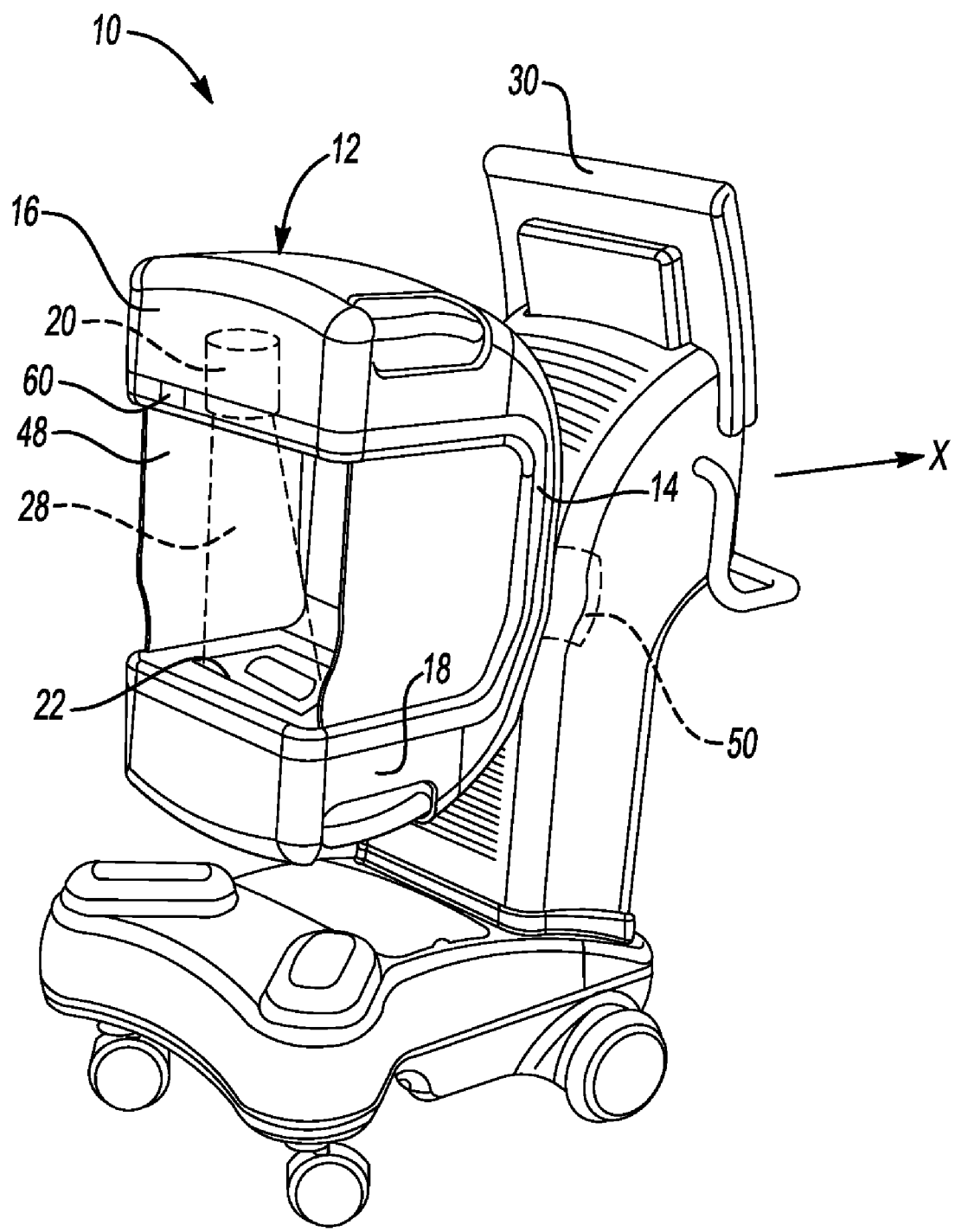
FIG. 1 illustrates a first embodiment of a CT scanner of the present invention including a camera that moves with a gantry.

FIG. 1 illustrates a CT scanner 10 of the present invention. The CT scanner 10 includes a gantry 12 that supports and houses components of the CT scanner 10. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses an x-ray source 20 that generate x-rays 28. In one example, the x-ray source 20 is a cone-beam x-ray source. The second arm 18 houses a complementary flat-panel detector 22. The x-rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray images at a plurality of rotational positions. Various configurations and types of x-ray sources 20 and detectors 22 can be utilized, and the invention is largely independent of the specific technology used for the CT scanner 10.

Figure 2:
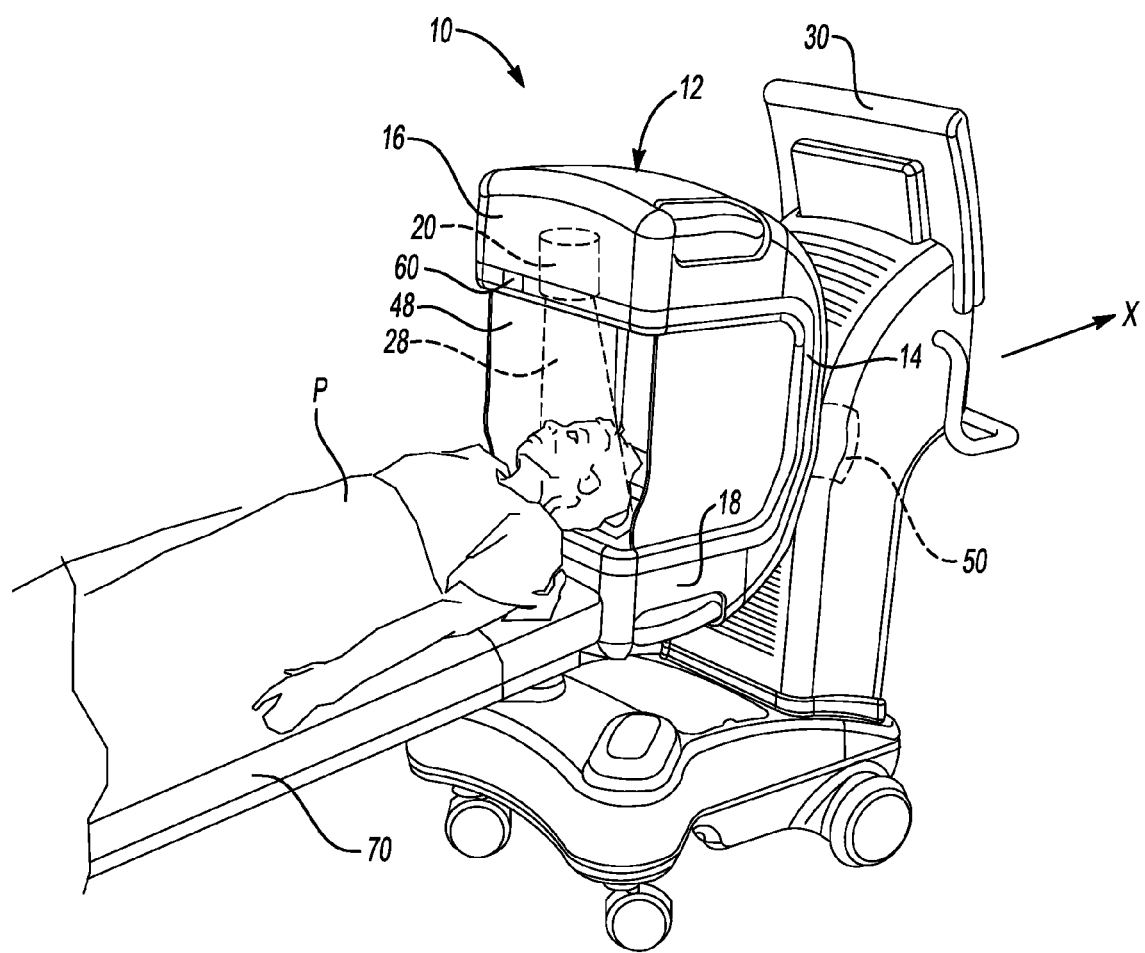
FIG. 2 illustrates the CT scanner of FIG. 1 with a part of a person received in the CT scanner.
Figure 3:
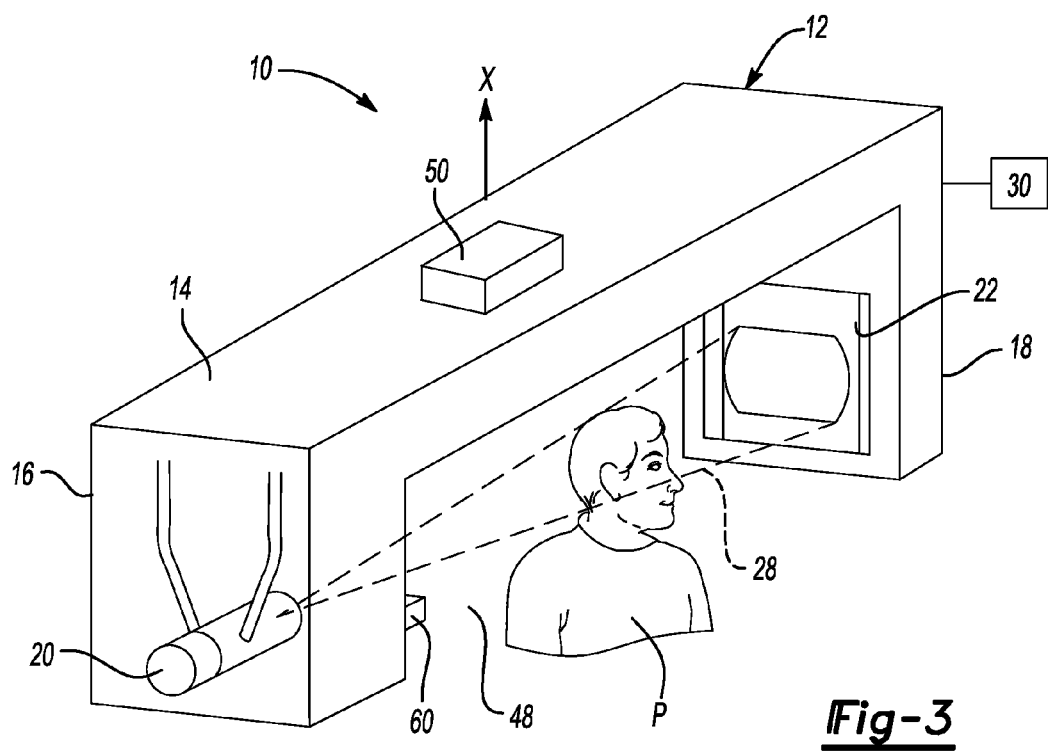
FIG. 3 illustrates a second embodiment of the CT scanner of the present invention including a camera that moves with a gantry.

FIG. 2 illustrates the CT scanner 10 with a part of the patient P received in a space 48 between the first arm 16 and the second arm 18. A motor 50 rotates the gantry 12 about an axis of rotation X to obtain a plurality of x-ray images of the patient P at the plurality of rotational positions. The axis of rotation X is positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal. In this example, the patient P is typically lying down on a table 70. Alternatively, as shown in FIG. 3, the axis of rotation X is substantially vertical. Typically, in this example, the patient P is sitting upright.

Figure 4:
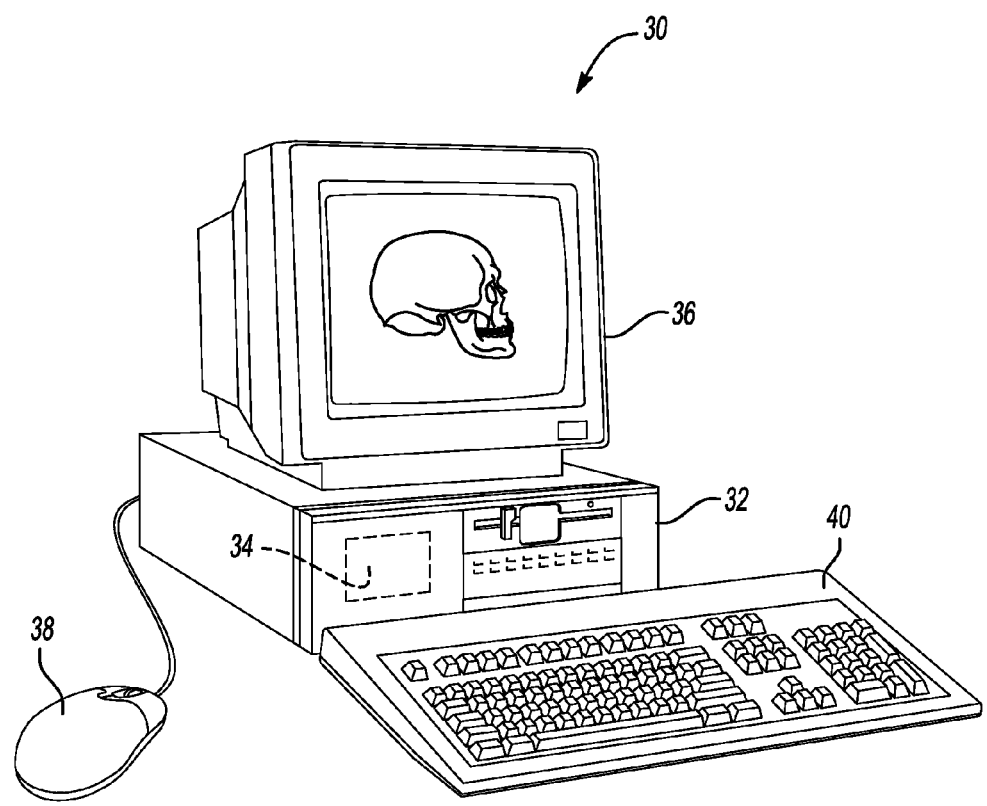
FIG. 4 illustrates a computer employed with the CT scanner of the present invention.

As shown schematically in FIG. 4, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 50. The plurality of x-ray images taken by the detector 22 are sent to the computer 30. The computer 30 generates a three dimensional CT image from the plurality of x-ray images utilizing any known techniques and algorithms. The three dimensional CT image is stored on the storage 34 of the computer 30 and can be displayed on the display 36 for viewing.

A camera 60 is mounted to the gantry 12 of the CT scanner 10. In one example, the camera 60 is a digital camera. For example, the camera 60 is a web camera. However, any type of camera 60 can be employed. In one example, the camera 60 is located on the first arm 16 near the x-ray source 20. However, the camera 60 can also be located on the second arm 18 near the detector 22.

In one example, as the gantry 12 rotates about the axis of rotation X, the camera 60 takes a photographic external image of the exterior of the patient P. The external images may each correlate to one of the x-ray images taken by the CT scanner 10. That is, the camera 60 captures an external image of the patient P at each of the plurality of rotational positions. This allows the camera 60 to record a real time image of the part of patient P that shows where the x-rays 28 from the x-ray source 20 are being directed.

Alternately, each of the external images does not correlate exactly to one of the x-ray images. However, the x-ray images and the external images are taken at known relative positions. The camera 60 takes numerous external images of the patient P as the gantry 12 rotates, and the computer 30 associates each of the external images to one of the x-ray images based on the known relative positions.

The external images are provided to the computer 30. A three dimensional external image is generated from the plurality of external images. The three dimensional external image is registered relative to the three dimensional CT image generated from the plurality of x-ray images. For example, the three dimensional external image and the three dimensional CT image are overlapped.

As the technician manipulates the three dimensional CT image, the technician can zoom in to view a specific area of the three dimensional CT image on the display 36 or rotate the three dimensional CT image to view the three dimensional CT image at a different orientation. If the technician zooms out and away from the three dimensional CT image, the three CT dimensional image on the display 36 can change into the corresponding three dimensional external image taken by the camera 60, providing the technician a reference image.

Alternately, both the three dimensional CT image and the corresponding three dimensional external image can be provided side by side on the display 36 simultaneously. This allows the technician to view an actual three dimensional external image of the part of the patient P that is subject to the x-rays 28 in addition to the three dimensional CT image of the part of the patient P generated by the CT scanner 10. As the technician manipulates the three dimensional CT image on the display 36, the corresponding three dimensional external image of the patient P taken by the camera 60 is also manipulated.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

The invention claimed is:

1. A scanner comprising:
    a gantry including a first arm section and a second arm section;
    an x-ray source mounted to the first arm section;
    an x-ray detector mounted to the second arm section;
    a camera mounted to one of the first arm section and the second arm section;
    a motor that rotates the gantry about an axis of rotation, wherein the x-ray detector takes a plurality of x-rays images and the camera takes a plurality of external images as the gantry rotates;
    a computer that generates a three dimensional CT image from the plurality of x-ray images and a three dimensional external image from the plurality of external images and stores the three dimensional CT image and the three dimensional external image; and
    a display that displays the three dimensional CT image, wherein the three dimensional CT image changes to the three dimensional external image as the three dimensional CT image is zoomed outwardly.

2. The scanner as recited in claim 1, wherein the scanner is a CT scanner.

3. The scanner as recited in claim 1, wherein the x-ray source is a cone beam x-ray source.

4. The scanner as recited in claim 1, wherein the camera is a digital camera.

5. The scanner as recited in claim 1, wherein the camera is a web camera.

6. The scanner as recited in claim 1, wherein the camera is mounted to the first arm section.

7. The scanner as recited in claim 1, further including a motor that rotates the gantry about an axis of rotation, wherein the x-ray detector takes a plurality of x-rays images and the camera takes a plurality of external images as the gantry rotates.

8. The scanner as recited in claim 1, wherein each of the plurality of external images correlates to one of the plurality of x-ray images.

9. The scanner as recited in claim 1, wherein the computer associates each of the plurality of external images to one of the plurality of x-ray images based on a known relative position.

10. The scanner as recited in claim 1, wherein the gantry has a substantially c-shape.

11. The scanner as recited in claim 1, wherein the first arm section and the second arm section are substantially parallel.

12. A method for capturing an image of a patient, the method comprising the steps of:
    mounting a camera on a gantry of a scanner;
    rotating the gantry about an axis of rotation;
    obtaining a plurality of x-ray images of the patient;
    generating a three dimensional CT image with the plurality of x-ray images;
    obtaining a plurality of external images of the patient;
    generating a three dimensional external image with the plurality of external images; and
    displaying the three dimensional CT image, zooming out from the three dimensional CT image, and changing the three dimensional CT image to the three dimensional external image.

13. The method as recited in claim 12, wherein the scanner is a CT scanner.

14. The method as recited in claim 12, further including the step of correlating each of the plurality of external images to one of the plurality of x-ray images.

15. The method as recited in claim 12, further including the step of associating each of the plurality of external images to one of the plurality of x-ray images based on a known relative position.

16. The method as recited in claim 12, wherein the step of mounting the camera on the gantry includes mounting the camera near an x-ray source.

* * * * *